United States Patent [19]

Higuchi et al.

[11] Patent Number: 4,470,980

[45] Date of Patent: Sep. 11, 1984

[54] METHOD OF INCREASING ORAL ABSORPTION OF β-LACTAM ANTIBIOTICS

[75] Inventors: Takeru Higuchi; Toshiaki Nishihata, both of Lawrence, Kans.

[73] Assignee: INTERx Research Corp., Lawrence, Kans.

[21] Appl. No.: 277,445

[22] Filed: Jun. 25, 1981

Related U.S. Application Data

[63] Continuation-in-part of Ser. No. 213,122, Dec. 5, 1980, abandoned, which is a continuation-in-part of Ser. No. 128,099, Mar. 7, 1980, abandoned.

[51] Int. Cl.$^3$ ............................................. A61K 31/62
[52] U.S. Cl. ................................... 424/232; 424/230; 424/231; 424/233; 424/234; 424/235
[58] Field of Search ............... 424/230, 231, 232, 233, 424/234, 235

[56] References Cited

U.S. PATENT DOCUMENTS 3,676,434  7/1972  Massey ........................... 424/246 X

OTHER PUBLICATIONS

Gibaldi, M., et al., *J. Pharm. Sci.,* 62(2), 343–344 (1973).
Imamura, Y., et al., *Chem. Pharm. Bull.,* (Japan), 22, 2324–2328 (1974).
Spector, R., et al., *J. Pharm. Exp. Ther.,* 188(1), 55–65 (1974).
Corell, T., et al., *Acta Pharmacol. et Toxicol.,* 45, 225–231 (1979).
*Chemical Abstracts,* 75: 60308q (1971) [Kaplan, D., *Chemotherapy,* 1971, 16(4), 252–258].
Chemical Abstracts, 83, 205953y (1975) Toyoshima et al., Insulin Complex Salts with Aminobenzoate Derivatives.
Chemical Abstracts, 71, 89823g (1969) Sugimoto, Isao Complexes XVI—Effect of Complex Formation on Drug Absorption etc.
Pharmaceutical Res. Laboratory, Yakugaku Zasshi, 88(5) 618–622 (1968), Studies on Complexes—Effect of Complex Formation on Drug Absorp. etc.
CA 69-65889 (17)—Complexes—Effect of Complex Formation on Drug Absorption from Alimentary Tract, Sugimoto, Isao et al., Tanabe Seiyaku Co. Ltd., Osaka, Yakugaku Zasshi V88F(6), pp. 690–694 (1968).
CA 69-50670 (13), Complexes, Effect of Complex Formation Drug Absorption from Alimentary Tract, Sugimoto, Isao, Tanabe Seiyaku Co. Ltd., Japan Pharm. Bull., 16(6), pp. 1098–1104 (1968).
CA 69-94857 (23), Complexes, Effect of Complex Formation on Drug Absorption from Alimentary Tract, Sugimoto, Isao, Tanabe Seiyaku Co. Ltd., Pharm. Res. Chem. Bull., 16(8), pp. 1527–1532 (1968).
CA 71-33382 (8), Complexes, Effect of Complex Formation on Drug Absorption from Alimentary Tract, Sugimoto, Isao, Tanabe Seiyaku Co. Ltd., Pharm. Res. Chem. Pharm. Bull., 17(5), pp. 994–998 (1969).
Shunji Ota Dept. Pharmacol. Showa Med. Col. Comments: Jap. 5 Pharm. 51, pp. 692–714 (1955), Influence of Various Substances on the Absorption of Histamine from the Large Intestine etc.
Microbiologic Pharmacologic Properties of New Ampicillin Deriv. etc., by Valcavi, R. Caponi et al., Arz. Forsch, 25(11), 1695–1697 (1975).
Journal of Pharmaceutical Sciences, vol. 57, No. 8, (1968), Reuning et al., Effect of Complex Formation on Drug Absorption etc., pp. 1335–1341.
Journal American Pharm. Assoc., No. 9, pp. 527–530, Investigation of Complex formed in Solution by Caffeine, Higuchi et al.

*Primary Examiner*—Richard A. Schwartz
*Attorney, Agent, or Firm*—Manfred Polk; Michael C. Sudol, Jr.

[57] ABSTRACT

A method and drug form are provided for increasing the oral absorption of β-lactam antibiotics such as the penicillins, cephalosporins and related chemical species by the oral administration of said β-lactam antibiotics in a suitable pharmaceutically accepted excipient to which has been added a hydroxy aryl or hydroxy aralkyl acid or salt, amide or ester thereof. The hydroxyaryl or hydroxyaralkyl acid or salt, amide or ester thereof is present in the drug form in quantities sufficient to be effective in enhancing the rate of oral absorption of the β-lactam antibiotic.

13 Claims, 2 Drawing Figures

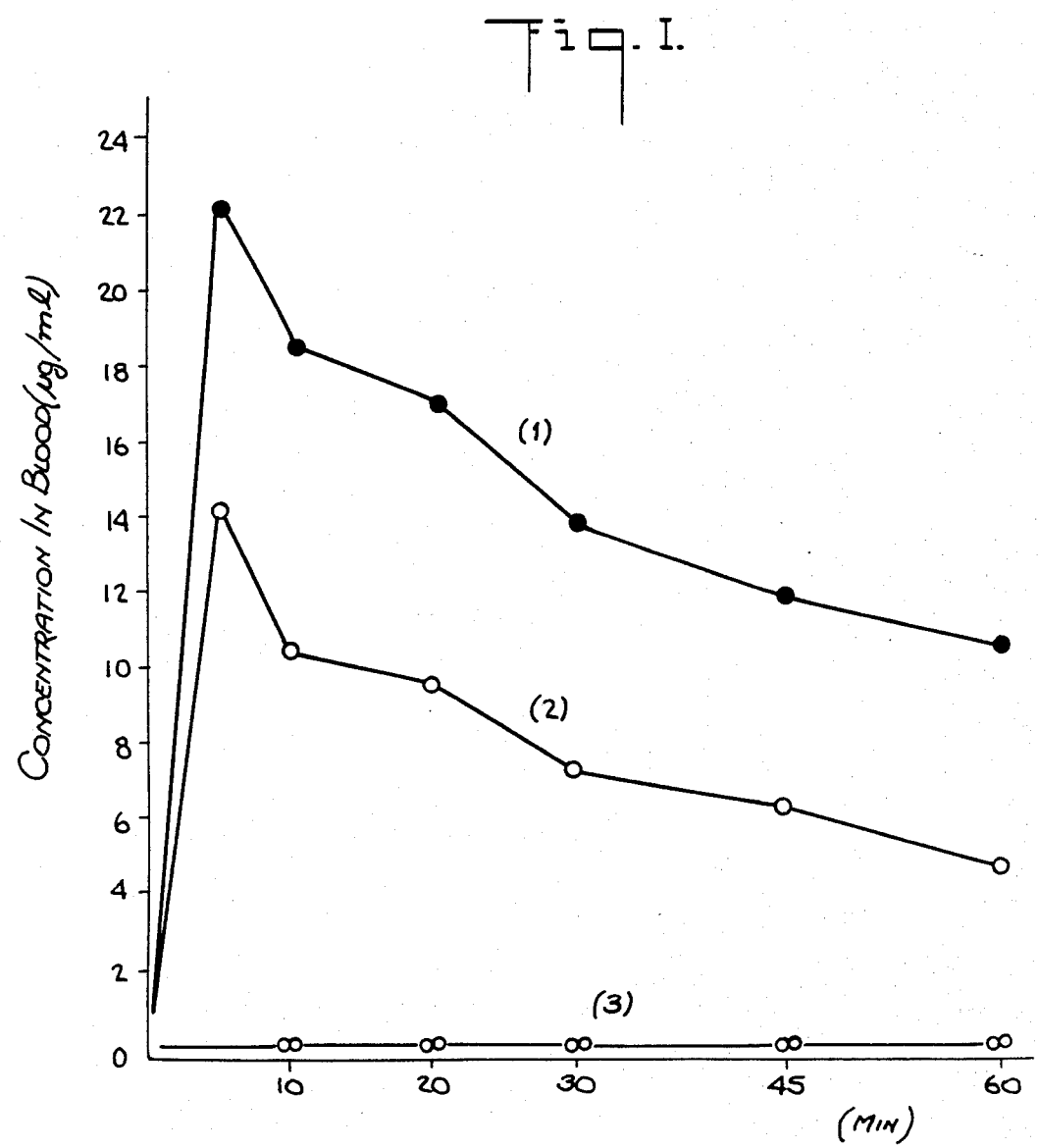

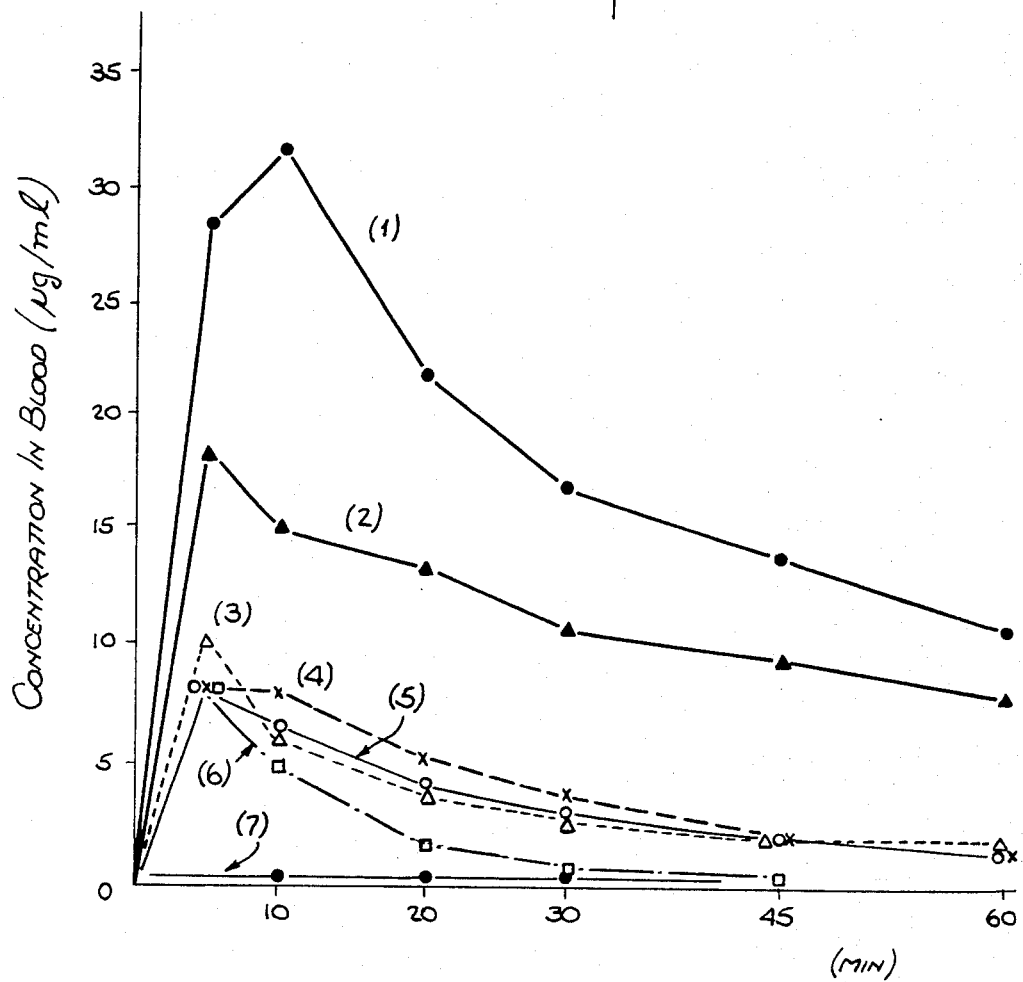
Fig. II.

METHOD OF INCREASING ORAL ABSORPTION OF β-LACTAM ANTIBIOTICS

CROSS REFERENCE TO RELATED APPLICATIONS

This application is a continuation-in-part of our previous application Ser. No. 213,122 filed Dec. 5, 1980 in the U.S. Patent and Trademark Office entitled Method of Increasing Oral Absorption of β-Lactam Antibiotics, now abandoned, which itself is a continuation-in-part of our previous application Ser. No. 128,099, filed Mar. 7, 1980, now abandoned in the U.S. Patent and Trademark Office entitled Method of Increasing Oral Absorption of β-Lactam Antibiotics.

BACKGROUND OF THE INVENTION

1. Field of the Invention

The present invention relates to the oral delivery of β-lactam antibiotics which by this route are poorly absorbed and more especially to the enhancement of this delivery by formulations which contain a hydroxyaryl or hydroxyaralkyl acid or salt, amide or ester thereof.

As employed in this application, the term "β-lactam antibiotics" refers to those antibiotics which contain the β-lactam moiety and include the penicillins, cephalosporins and related chemical species.

2. Description of the Prior Art

It is well known to this art that the β-lactam antibiotics which have the common structural feature, a four-member lactam ring, have been described as the most important class of therapeutic agents to combat gram-positive and gram-negative infections. Inspite of their great popularity, it is also well known that a number of the β-lactam antibiotics such as the penicillins, penicillin G, methacillin and carbenicillin, and the cephalosporins, cefaxolin, cephapirin, cephaloridine, cephalothin, cephapirin, cephanone, cefamandole, cefaporole, cefoxitin, cephacetrile, cefmetazole, cefuroxime, cefotaxime, T-1551, the oxacephalosporin, S-6059, ampicillin and amoxicillin show poor oral activity.

The penicillins, which were introduced a number of years ago, suffer from two major disadvantages: poor activity against resistant organisms and lack of oral activity which is due to its inherent instability to gastric acid. The acid instability was partially overcome by the discovery of more acid stable penicillins such as penicillin V, which permit the penicillin to be adsorbed with less degradation and hence produce higher blood levels of the active therapeutic agent. However, in spite of these chemical modifications to produce acid stable, orally effective penicillins, many of the penicillins in clinical use, such as penicillin G, methacillin, carbenicillin and ticarcillin, cannot be administered by the oral route. Even the newer esters of carbenicillin, carfecillin and carindacillin are only 40% absorbed and give low blood levels of carbenicillin.

The second major problem with penicillin antibiotics is their lack of activity against resistant strains of bacteria which produce the degrading enzyme, penicillinase. The earlier semisynthetic penicillins, such as methicillin, oxacillin, cloxacillin, dicloxacillin, flucloxacillin and nafcillin, were developed to overcome this problem. This class of penicillins were resistant to the penicillinase enzyme and were active against those resistant organisms which produce the enzyme. However, these compounds were less active than their parents and in particular showed poor activity against the important gram-negative organisms.

The second class of β-lactam antibiotics, the cephalosporins, were developed because they, unlike the penicillins, were very active against both the penicillinase producing gram-positive bacteria and the gram-negative bacteria. However, lack of oral activity, an almost universal characteristic of the cephalosporins, is shared by the parent molecule, cephalosporin C, and most of the newer semisynthetic analogues. This lack of oral activity was totally unexpected because the cephalosporins, unlike the penicillins, are stable in gastric acid. Since the molecule is excreted unchanged in the feces, it is apparent that the lack of oral activity is due to poor absorption and is probably caused by the polar nature of the cephalsoporin nucleus. Through chemical modification a number of orally effective β-lactam antibiotics were prepared, such as cephalexin, cephradine, cephaloglycin, cefdioxil and cefaclor, which have been shown to be greater than 80% absorbed. Unfortunately, they are much less active in vitro than the clinically injectable cephalosporins. It is clear that this chemical modification has produced an orally active antibiotic whose antibacterial properties are inferior to those of the currently used injectable cephalosporins.

Thus, there exists a clear and present need for a novel method to enhance the oral absorption of the non-orally effecitive β-lactam antibiotics. Said method would permit the oral use of the clinically important β-lactam antibiotics whose use is presently limited to intramuscular and intravenous administration.

SUMMARY OF THE INVENTION

Accordingly, a major object of this invention is to provide a novel class of agents which enhance the oral absorption of β-lactam antibiotics.

Another object is to provide a process utilizing said novel class of agents to enhance the oral absorption of β-lactam antibiotics.

Another object is to provide a stable drug form utilizing said novel class of agents which when administered orally will provide increased blood levels of the therapeutic agent.

Other objects, features and advantages of the invention will be apparent to those skilled in the art from the detailed description of the invention which follows.

All of the foregoing objects are readily attained by providing a method and drug form wherein the oral absorption of β-lactam antibiotics is enhanced, the method comprising the steps of preparing a drug form suitable for oral delivery, and a drug form comprising an effective unit dosage amount of the β-lactam antibiotic, a hydroxyaryl or hydroxyaralkyl acid or salt, amide or ester thereof, the latter adjuvants being present in said drug form in an amount sufficient to be effective in enhancing the rate of the oral absorption of the antibiotic, and a suitable pharmaceutically accepted excipient.

DETAILED DESCRIPTION OF THE INVENTION

The present invention, generally, comprises the steps of preparing a drug form capable of being orally administered, wherein the drug form comprises an effective unit dosage amount of a β-lactam antibiotic and hydroxy aryl or hydroxyaralkyl acids or salts, amides or esters thereof, the hydroxy aryl or hydroxy aralkyl acid or salts, amides and esters thereof being present in the drug form in a sufficient quantity to be effective in enhancing the oral absorption rate and administering the drug form to warmblooded animals. The amount of β-lactam antibiotic varies over a wide range, but generally any therapeutically effective unit dosage amount of the selected β-lactam antibiotic is used.

The hydroxy aryl or hydroxy aralkyl acids or their salt, amide and ester forms that are used as the adjuvants in our method and in our drug forms have the following structural formulae including the various isomers possible within the formulae set forth:

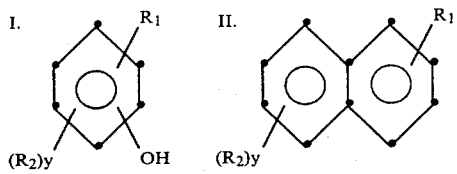

wherein $R_1$ is a radical selected from $—CO_2H$, $—(CH_2)_n—COOH$, $—CH=CH—CO_2H$,

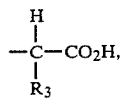

$—SO_3H$, $CH_2SO_3H$, $X(CH_2)_nCO_2H$, $SO_2NHR_4$, $PO(OH)N(OH)_2$, $PO(OH)OR_4$, or a pharmaceutically acceptable salt thereof wherein $R_2$ is a radical selected from OH, H, a lower alkoxy radical having 1–10 carbon atoms, a lower alkyl radical having 1–10 carbon atoms, a lower alkenyl radical having 2–5 carbon atoms, a lower alkanoyl radical having 1–5 carbon atoms, a lower alkanoyloxy radical having 1–5 carbon atoms, a carboxy radical, a carbo-lower alkoxy radical having 1–5 carbon atoms, a halo radical, a mono-, di-, or tri-halo lower alkyl radical having 1–5 carbon atoms, an amino radical, a mono- or di-lower alkyl amino radical having 1–5 carbon atoms, a carbamyl radical, a lower mono- or di-alkyl carbamyl radical wherein the alkyl group has 1–5 carbon atoms, a thio radical, a lower alkyl thio radical wherein the alkyl group has 1–5 carbon atoms, a cyano radical, a lower alkyl sulfone radical wherein the alkyl group has 1–5 carbon atoms, a lower alkyl sulfoxide radical wherein the alkyl group has 1–5 carbon atoms, a nitro radical, $N(CN_2)_2$, $C(CN)_3$, an alkynyl radical having 2–6 carbon atoms, a cycloalkyl radical having 3–10 carbon atoms, a cycloalkenyl radical having 3–10 carbon atoms, an aryl radical including phenyl, a heteroaryl radical including thiophenyl and imidazolyl, or a heterocycloalkyl radical including morpholinyl and piperidinyl, wherein $R_3$ is a straight or branched alkyl radical having 1–6 carbon atoms or a hydroxy radical, wherein $R_4$ is H or a lower alkyl radical having 1–5 carbon atoms, wherein X is 0 or S, wherein n is an integer of 0–5, wherein y is 1 or 2, and when y is 2, both the $R_2$ radicals, taken together, can form a ring containing O, N or S.

More preferred adjuvants are those having the formula:

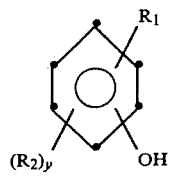

wherein $R_1$ is a radical selected from $—CO_2H$, $—(CH_2)—COOH$, $—CH=CH—CO_2H$,

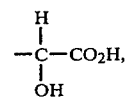

$—SO_3H$, $—CH_2SO_3H$, $O(CH_2) CO_2H$ or a pharmaceutically acceptable salt thereof wherein $R_2$ is selected from OH, H, a lower alkoxy radical having 1–10 carbon atoms, a lower alkyl radical having 1–10 carbon atoms, a halo radical, a mono-, di-, or tri-, halo lower alkyl radical wherein the alkyl group has 1–5 carbon atoms, a lower alkyl thio radical wherein the alkyl radical has 1–5 carbon atoms, a cycloalkyl radical having 3–10 carbon atoms, or a cycloalkenyl radical having 3–10 carbon atoms and wherein y is an integer of 1 or 2.

Highly preferred adjuvants are those having the formula:

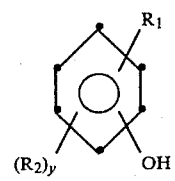

wherein $R_1$ is $CO_2H$, $—(CH_2)—COOH$,

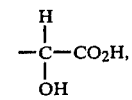

$SO_3H$, or a pharmaceutically acceptable salt thereof wherein $R_2$ is OH, H, a lower alkoxy radical, including methoxy, ethoxy, butoxy, or octyloxy, a lower alkyl radical including methyl, isopropyl, ethyl, t-butyl, n-butyl, or t-octyl, a halo radical, or a tri-halo lower alkyl radical including trifluoromethyl, and wherein y is an integer of 1 or 2.

Specific adjuvants useful in our method and drug forms for enhancing oral absorption of β-lactam antibiotics include salicylic acid, 5-methoxy salicylic acid, 3,4-dihydroxy phenyl acetic acid (DOPAC) and homovanillic acid and their sodium salts thereof. Other hydroxyaryl acids, such as 1-hydroxy-2-naphthoic acid, naphthoresorcyclic acid, ferulic acid, caffeic acid, resorcylic acid and gentisic acid, have similar useful adjuvant activity in our process. Such adjuvants are not considered novel per se and may be prepared by techniques known to those skilled in the art.

The amount of hydroxyaryl or hydroxyaralkyl acid or salt, amide or ester derivatives thereof used in our method and drug forms may vary over a wide range; in general, the identity and the amount of the hydroxyaryl or hydroxyaralkyl acids or salt, amide or ester thereof is used in connection with the drug in order to be effective in enhancing the absorption rate of the drug from the gastrointestinal compartment into the bloodstream. The effectiveness of the hydroxyaryl or hydroxyaralkyl acid or salt, amide or ester derivatives thereof becomes significant at local concentration exceeding 0.01% at the absorption site. Their use at a dosage whereby their concentration at the absorption site exceeds 5% is not recommended because of the local irritating effect on the tissue.

Generally the amount of adjuvant in our drug forms is from 50-500 mg in each unit dose, per drug form (tablet, capsule or the like). The percentage of adjuvant in the total combination of drug plus adjuvant is 20-95% with a preferred ratio of adjuvant in the total combination of drug plus adjuvant being 30-60%. A most preferred ratio of adjuvant to adjuvant plus drug is 50%.

The β-lactam antibiotics whose enhanced oral delivery is a subject of the present invention encompass both the penicillins, penicillin G, methacillin, carbenicillin and ticaricillin, and the cephalosporins, cephalosporin C, cefazolin, cephapirin, cephaloridine, cephalothin, cephapirin, cephanone, cefamandole, cefaparole, cefoxitin, cephacetrile, cefmetazole, cefoxitin, cefuroxime, cefotaxime, T-1551, and the oxacephalosporin, S-6059. The quantity of β-lactam antibiotic necessary for preparing the drug form could vary over a wide range but would normally be regulated by that quantity necessary to comprise the therapeutically effective unit dosage.

EXAMPLE 1

The sodium salt of cefmetazole (50 mg/kg) and sodium salicylate (200 mg/kg) dissolved in water were given to mice by gavage. As a control, mice were given an equal dose of the sodium salt of cefmetazole in water without the added sodium salicylate. The mice were place in individual metabolism cages and their urines collected after 24 hours.

The urine samples were acidified to pH 2.0 with 1N phosphoric acid. Acidified samples were applied to 100-200 mesh XAD.2 columns (1.5 ml), and the column washed with $H_2O$. Cefmetazole was eluted with 2 ml methanol and measured by high pressure liquid chromatography which was carried out using an Altex liquid chromatograph equipped with a dual wavelength recorder (254 nm and 280 nm). The column was a Li-Chrosorb 10 RP-18 (length=25 cm., internal diameter—4.6 mm) obtained from Chrompack, Whittier, CA. All assays were done at ambient temperatures. A 3 cm guard column of RP-18 column material (Rheodyne, Inc., Berkeley, CA) was also used. The mobile phase consisted of 30% tetrahydrofuran, $7.5 \times 10^{-4}M$ tetra-n-hexyl ammonium perchlorate, and 70% $H_2O$. The flow rate was 2 ml/min and the pressure less than 2000 psi. Concentrations of cefmetazole were determined by measuring peak height at 254 nm and evaluating on the basis of standard curves run under identical conditions. The results are shown in Table I.

TABLE I

| Urine Levels of Cefmetazole | | |
|---|---|---|
| | Number of Mice | Percent of Dose In Urine |
| Cefmetazole 50 mg/kg + sodium salicylate 200 mg/kg | 22 | 70.8 ± 11.9 |
| Cefmetazole 50 mg/kg | 8 | 9.1 ± 7.5 |

TABLE I-continued

| Urine Levels of Cefmetazole | | |
|---|---|---|
| | Number of Mice | Percent of Dose In Urine |
| Standard deviation | | |

In like manner the following combinations of other β-lactams and hydroxyaryl acids were also found to enhance the oral absorption of the corresponding antibiotic.

| Example | β-lactam Antibiotic | Hydroxyaromatic Acid |
|---|---|---|
| 2 | penicillin G. | salicylic acid |
| 3 | methacillin | sodium salicylate |
| 4 | carbenicillin | gentisic acid |
| 5 | ticaricillin | ferulic acid |
| 6 | methacillin | naphthoresorcyclic acid |
| 7 | ticaricillin | caffeic acid |
| 8 | carbenicillin | sodium salicylate |
| 9 | penicillin G | hydroxy-2-naphthoic acid |
| 10 | carbenicillin | resorcyclic acid |
| 10A | ampicillin | salicylic acid |
| 10B | amoxicillin | salicylic acid |
| 11 | cephalosporin C | salicylic acid |
| 12 | cefazolin | sodium salicylate |
| 13 | cefuroxine | gentisic acid |
| 14 | cephaprin | homovanellic acid |
| 15 | cephaloridine | sodium salicylate |
| 16 | cephmetazole | homovanillic acid |
| 17 | cephapirin | ferulic acid |
| 18 | cephanone | salicylic acid |
| 19 | cefmetazole | salicylic acid |
| 20 | cefaparole | sodium salicylate |
| 21 | cefoxitin | naphthoresorcyclic acid |
| 22 | cephacetrile | gentisic acid |
| 23 | cefmetazole | caffeic acid |
| 24 | cefoxitin | resorcyclic acid |
| 25 | cefuroxime | sodium salicylate |
| 26 | cefotaxime | ferulic acid |
| 27 | T-1551 | homovanillic acid |
| 28 | S-6059 | caffeic acid |
| 29 | cefmetazole | 1-hydroxy-2-naphthoic acid |
| 30 | cefamandole | gentisic acid |
| 31 | cephalothin | salicylic acid |

TABLE II

Absorption of β-Lactam Antibiotics in the Presence of Various Adjuvants

Increase in absorption by the use of the adjuvants of this invention was also studied in dogs and rats under the conditions described below. cl Experiments in Dogs Animal: Beagles (body weight 9.9-12.0 kg), 2 animals per test
Drug: β-Lactam antibiotics
Adjuvant: Hydroxylated aromatic carboxylic acids
Dose: β-Lactam antibiotic/adjuvant=300 mg/300 mg/kg
Form of inoculum: Capsule
Route of administration: Per os
Blood sampling: Vein (upper arm)
Object of assay: Blood level
Quantitation: Carbenicillin was determined by bioassay. Other cephalosporin compounds were studied by HPLC.

Experiments in Rats

Animal: Male rats (body weight 275-300 g), 2 animals per test
Drug: Cephalosporin compounds
Adjuvant: Hydroxylated aromatic carboxylic acids Dose: β-Lactam antibiotic/adjuvant=30 mg/50 mg/kg
Form of inoculum: Dissolved in 0.05M $NaH_2PO_4$ or 0.1N NaOH, with subsequent pH adjustment with phosphoric acid.
Route of administration: Intraduodenal after ligation of the pylorus
Blood sampling: 0.3 ml from jugular vein
Quantitation: HPLC The blood levels of Cefoxitin with and without DOPAC are shown in FIG. 1. Curves (1) and (2) represent the concentrations of Cefoxitin (30 mg/kg) when administered together with 3,4-dihydroxy phenyl acetic acid (DOPAC) (50 mg/kg) in two rats, while curve (3) shows the values in a control animal given 30 mg/kg Cefoxitin alone. FIG. 2 shows similar curves obtained with various cephalosporin compounds and represent average values. Curve (1) was obtained with cephazolin, (2) with Cefoxitin (3) with 6059-S, (4) with YM-09330, (5) with Cephmetazole, and (6) with Cefalotin. Curve (7) represents average values for controls which received antibiotics (1)–(6) alone.

The results obtained in similar experiments are shown in Table 2. In the table, $(AUC)_o$ represents the area below the blood level curve, indicating the degree of absorption of the drug. The $(AUC)_o$ values for all controls were approximately 0, showing that in the absence of the adjuvant or promoting agent there was virtually no absorption.

by combining the β-lactam antibiotic in a therapeutic amount and the hydroxyaromatic acid or salt thereof in sufficient quantity to be effective to enhance oral delivery with any oral pharmaceutically acceptable inert carrier, such as lactose, starch (pharmaceutical grade), dicalcium phosphate, calcium sulfate, Kaolin, mannitol and powdered sugar. In order to reduce the irritation in the stomach, the preferred dose form of the hydroxyaromatic acid should be pharmaceutically acceptable salt and the drug form should be designed to release the β-lactam antibiotic and the hydroxyaromatic acid salt beyond the pylorus. In addition, when required, suitable binders, lubricants, disintegrating agents, and coloring agents can also be added. Typical binders include, without limitation, starch, gelatin, sugars such as sucrose, molasses, and lactose, natural and synthetic gums, such as acacia, sodium alginate, extract of Irish moss, carboxymethylcellulose, methylcellulose, and polyvinylpyrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose and wood products, alginic acid, guar gum, citris pulp, carboxymethylcellulose, and sodium lauryl sulfate. Optionally, if desired, a conventionally, pharmaceutically acceptable dye can be incorpo-

| Example | β-Lactam Compound | Absorption Promotor | $(AUC)^o$ (μg/hr/ml) | Experimental Animal |
|---|---|---|---|---|
| 32 | Cefoxitin | DOPAC* | 10.3 | Dog |
| 33 | Cefoxitin | 5-Methoxy-salicylate Na | 13.1 | Dog |
| 34 | Cefoxitin | Caffeic acid | 4.0 | Dog |
| 35 | Cephmetazole | DOPAC | 7.2 | Dog |
| 36 | Cefoxitin | DOPAC | 10.3 | Dog |
| 37 | Cephazolin | DOPAC | 10.9 | Dog |
| 38 | Cefalotin | DOPAC | 2.7 | Dog |
| 39 | Cefoxitin | DOPAC | 25.9 | Rat |
| 40 | Cefoxitin | Homogentisic acid | 10.3 | Rat |
| 41 | Cefoxitin | Homovanillic acid | 6.0 | Rat |
| 42 | Cefoxitin | Gentisic acid | 7.6 | Rat |
| 43 | Cefoxitin | β-Resorcylic acid | 1.9 | Rat |
| 44 | Cefoxitin | Caffeic acid | 0.5 | Rat |
| 45 | Cefoxitin | Ferulic acid | 1.1 | Rat |
| 46 | Cefoxitin | Oxy-2-naphthoic acid | 0.4 | Rat |
| 47 | Cephmetazole | DOPAC | 4.1 | Rat |
| 48 | Cephazolin | DOPAC | 48.2 | Rat |
| 49 | Cefalotin | DOPAC | 1.7 | Rat |
| 50 | 6059-S | DOPAC | 6.7 | Rat |
| 51 | YM-09330 | DOPAC | 6.3 | Rat |
| 52 | Carbenicillin | DOPAC | 7.9 | Dog |
| Control | Carbenicillin | None | 5.2 | Dog |
| Control | Individual cephalosporins | None | 0 | Dog, rat |

*3,4-Dihydroxyphenylacetic acid

BRIEF EXPLANATION OF THE FIGURES

FIG. 1 shows blood levels of Cefoxitin (30 mg/kg) and DOPAC (50 mg/kg) administered to rats, curve (1) and curve (2) representing findings when the two agents were given simultaneously and curve (3) the levels of Cefoxitin given by itself. FIG. 2 shows the blood levels of various cephalosporin compounds administered in the same manner, curve (1) representing the values for Cefazolin, curve (2) of Cefoxitin, curve (3) of 6059-S, curve (4) of M-09330, curve (5) of Cephmetazole, curve (6) of Cefalotin, and (7) of controls.

The drug forms of this invention are suitably administered in oral dosage form, such as by tablet or capsule, rated into the oral dosage unit form, e.g., any of the standard FD&C dyes.

EXAMPLE 53

Preparation of Sodium 2-hydroxy-5-methoxy benzenesulfonate p-Methoxyphenol (12.4 g) was dissolved in chloroform (100 ml) and cooled in ice. Chlorosulfonic acid (11.6 g) was added dropwise to the stirred reaction mixture. The cooling bath was removed after the addition and stirring continued for 24 hours at room temperature. The chloroform was then evaporated off and the residue was vacuum dried to a hygroscopic light brown solid weighing 20.5 g which was 2-hydroxy-5-methoxybenzenesulfonic acid. NMR (CDCl$_3$) 3.73 (3H, s, OCH$_3$), 6.8–7.2 (3H, m, aromatic H̱), and 9.86 (2H, broad s, OH̱and SO$_3$H̱). IR (film) 3500–2900, 1512, 1470, 1229, 1198, 996, 938 cm$^{-1}$.

The above sulfonic acid (10 g) was dissolved in water (10 ml) and poured into 75 ml of saturated sodium chloride solution. A white solid separated immediately. It was filtered and dried. Crystallization from water gave the pure sodium salt of 2-hydroxy-5-methoxybenzenesulfonic acid (6.6 g). NMR (D$_2$O) 3.83 (3H, s, OCH$_3$), 7.05 and 7.33 (3H, multiplets, aromatic). IR (KBr) 3260, 1518, 1440, 1300, 1280, 1240, 1210, 1905, 1045 cm$^{-1}$.

EXAMPLE 54

Typical preparation of enteric-coated tablets containing adjuvant.

| 300 mg Cefoxitin Tablets | |
|---|---|
| Ingredient | Amount per Tablet |
| Cefoxitin (sodium salt) | 300 mg |
| Sodium 5-methoxysalicylate | 300 mg |
| Microcrystalline cellulose | 70 mg |
| Magnesium stearate | 30 mg |
| Total | 700 mg |

The cefoxitin sodium salt was ground, passed through a 40 mesh screen, mixed with the sodium 5-methoxysalicylate, ½ the magnesium stearate and slugged with ⅞″ flat punches. The slugs were broken up and passed through a 40 mesh screen, mixed with microcrystalline cellulose and the remaining magnesium stearate. The material was tableted using 7/16″ deep concave punches to give tablets of 10 Kg hardness.

Coating

The tablets were coated with 15 mg pre-coat and 34 mg enteric coat according to the coating procedure described below.

Enteric Coating Procedure

Tablets or capsules were placed in a coating pan containing baffles to provide adequate tumbling. A small amount of the coating solution was applied using an air sprayer and the solvents evaporated with a warm air supply directed into the coating pan. This procedure was repeated until the desired amount of coating material was applied. The amount of coating material was determined from the weight gain of a representative group of tablets.

Coating Solutions

Pre-coat: A film of hydroxypropylmethylcellulose was applied to the tablets followed by an enteric coating.

Enteric coat: A film of hydroxypropylmethylcellulosephthalate was applied.

Solutions: A 5% by weight solution of hydroxypropylmethylcellulose and a 10% by weight solution of hydroxypropylmethylcellulosephthalate in ethanol:methylene chloride (1:1 by weight) were used as the coating solutions.

EXAMPLE 55

Following the procedure of Example III for the preparation of enteric-coated tablets and using equivalent quantities of ingredients, the following compounds can be substituted for cefoxitin which is (6R-cis)-3-[[(aminocarbonyl)oxy]methyl]-7-methoxy-8-oxo7[(2-thienylacetyl)-amino]-5-thia-1-azabicyclo [4.2.0]oct-2-ene-2-carboxylic acid.

(1) Cephamandole which is 7-[(hydroxyphenylacetyl)-amino]-3-[[(1-methyl-1H-tetrazol-5-yl)thio]methyl]-8-oxo-5-thia-1-azabicyclo[4.2.0]oct-2-ene-2-carboxylic acid.

(2) Amoxicillin which is 6-[[amino(4-hydroxyphenyl)-acetyl]amino]-3,3-dimethyl-7-oxo-4-thia-1-azabicyclo-[3.2.0]heptane-2-carboxylic acid (3) N-formimidoyl thienamycin monohydrate.

Also the following adjuvants may be used in combination with any of the drugs or compounds shown in Examples 1 to 54 in appropriate ratios. The adjuvants may be chosen from the following salts or the corresponding acids:

Sodium-5-methoxysalicylate
Sodium salicylate
Sodium homovanilate
Sodium 2,5-dihydroxybenzoate
Sodium 2,4-dichydroxybenzoate
Sodium 3,4-dihydroxymandelate
Sodium 3-methoxy-4-hydroxymandelate
Sodium 3-methoxy-4-hydroxycinnamate
Sodium 5-methoxy-2-hydroxyphenylsulfonate
Sodium 3-methylsalicylate
Sodium 5-methylsalicylate
Sodium 5-tert-octylsalicylate
Sodium 3-tert-butyl-6-methylsalicylate
Sodium 3,5-diisopropylsalicylate
Sodium 3-tert-butyl-5-methylsalicylate
Sodium guaicolsulfonate
Sodium 5-bromosalicylate
Sodium 3,5-dibromosalicylate
Sodium 5-iodosalicylate
Sodium 3,5-diiodosalicylate
Sodium 2-hydroxyphenylacetate
Sodium 3-hydroxy-2-naphthoate
Sodium mandelate
Sodium phenyllactate
Sodium 2-hydroxyphenylmethanesulfonate
Sodium 5-trifluoromethyl-2-hydroxybenzoate
Sodium 4-hydroxy-3-hydroxyphenylmethanesulfonate
Sodium 3-methoxysalicylate
Sodium 5-octyloxysalicylate
Sodium 5-butoxysalicylate
Sodium p-hydroxyphenoxyacetate
Sodium 3,4-dihydroxyphenylacetate
Sodium 5-chlorosalicylate
Sodium 3,4-dihydroxycinnamate
Sodium 3,5-dihydroxybenzoate
Sodium 2-hydroxy-3-methoxybenzoate
Sodium 1-hydroxy-2-naphthoate
Sodium salicylurate Any skilled artisan concerned with the subject matter of this invention, can prepare these oral dosage forms by simply referring to the oral dosage form preparatory procedure outlined in REMINGTON'S PHARMACEUTICAL SCIENCES, Fifteenth Edition (1975), pages 1576 through 1617 inclusive.

From the foregoing description, one of ordinary skill in the art can easily ascertain the essential characteristics of this invention, and without departing from the spirit and scope thereof, can make various changes and modifications of the invention to adapt it to various usages and conditions. As such, such changes and modifications are properly equitably, and intended to be, within the full range of equivalence of the following claims.

What is claimed is:

1. A method for enhancing the rate of absorption of an orally administered β-lactam antibiotic into the bloodstream, said method comprising the steps of preparing a drug form capable of being orally absorbed, said drug form comprising a therapeutically effective dosage amount of the β-lactam antibiotic and an adjuvant of the formula:

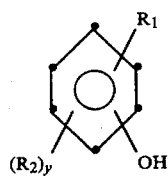

wherein $R_1$ is $CO_2H$, $(CH_2)COOH$,

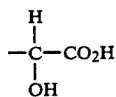

or $SO_3H$, or a pharmaceutically acceptable salt thereof wherein $R_2$ is OH, H, a lower alkoxy radical, a lower alkyl radical, a halo radical, or a tri-halo lower alkyl radical, and wherein y is an integer of 1 or 2, said adjuvant being present in said drug form in a sufficient amount to be effective in enhancing said oral absorption rate, and administering said drug form orally.

2. The method of claim 1 wherein said β-lactam antibiotic is a penicillin, a cephalosporin, or thienamycin.

3. The method of claim 2 wherein said penicillin is penicillin G, methacillin, carbenicillin, tricaricillin, amoxicillin or ampicillin.

4. The method of claim 2 wherein said cephalosporin is cephalosporin C, cefazolin, cephapirin, cephaloridine, cephalothin, cephapirin, cephanone, cefamandole, cefaparole, cefoxitin, cephacetrile, cefmetazole, cefuroxime, cefotaxime, T-1551 or S-6059.

5. The method of claim 1 wherein said β-lactam antibiotic is thienamycin or a derivative thereof.

6. The method of claim 5 wherein the derivative is N-formimidoyl thienamycin monohydrate.

7. The method of claim 2 wherein said β-lactam antibiotic is cefoxitin.

8. The method of claim 2 wherein said β-lactam antibiotic is ampicillin.

9. The method of claim 2 wherein the said β-lactam antibiotic is amoxicillin.

10. The method of claim 2 wherein the said β-lactam antibiotic is cefmetazole.

11. The method of claim 1 wherein said adjuvant is 5-methoxysalicylic acid, salicylic acid, homovanillic acid; 2,5-dihydroxybenzoic acid; 2,4-dihydroxybenzoic acid; 3,4-dihydroxymandelic acid; 5-methoxy-2-hydroxy-phenylsulfonic acid; 3-methylsalicylic acid; 5-methylsalicylic acid; 5-tert-octylsalicylic acid; 3-tert-butyl-6-methylsalicylic acid; 3,5-diisopropylsalicylic acid; 3-tert-butyl-5-methylsalicylic acid; guaicolsulfonic acid; 5-bromosalicylic acid; 3,5-dibromosalicylic acid; 5-iodosalicylic acid; 3,5-diiodosalicylic acid; 2-hydroxyphenylacetic acid; 2-hydroxyphenylmethanesulfonic acid; 5-trifluoromethyl-2-hydroxybenzoic acid; 4-hydroxy-3-hydroxyphenylmethanesulfonic acid; 3-methoxysalicylic acid; 5-octyloxysalicylic acid; 5-butoxysalicylic acid; p-hydroxyphenoxyacetic acid; 3,4-dihydroxyphenylacetic acid; 5-chlorosalicylic acid; 3,5-dihydroxy-benzoic acid; 2-hydroxy-3-methoxybenzoic acid; or the sodium salts thereof.

12. The method of claim 1 wherein the adjuvant is salicylic acid or sodium salicylate.

13. A method for enhancing the rate of absorption of an orally administered cefoxitin into the blood stream, said method comprising the steps of preparing a cefoxitin drug form being capable of being orally absorbed, said drug form comprising a therapeutically effective dosage amount of cefoxitin and an adjuvant selected from the group consisting of sodium salicylate and sodium 5-methoxy salicylate, said adjuvant being present in said drug form in a sufficient amount to be effective in enhancing said oral absorption rate and administering said drug form orally.

* * * * *